United States Patent
Nord et al.

(10) Patent No.: US 7,933,380 B2
(45) Date of Patent: Apr. 26, 2011

(54) RADIATION SYSTEMS AND METHODS USING DEFORMABLE IMAGE REGISTRATION

(75) Inventors: Janne Ilmari Nord, Espoo (FI); Jarkko Yrjana Peltola, Tuusula (FI)

(73) Assignee: Varian Medical Systems International AG (CH)

( * ) Notice: Subject to any disclaimer, the term of this patent is extended or adjusted under 35 U.S.C. 154(b) by 810 days.

(21) Appl. No.: 11/863,876

(22) Filed: Sep. 28, 2007

(65) Prior Publication Data
US 2009/0087124 A1   Apr. 2, 2009

(51) Int. Cl.
*A61N 5/10* (2006.01)
*G21K 5/10* (2006.01)

(52) U.S. Cl. ............................. 378/65; 378/68; 378/69

(58) Field of Classification Search .............. 378/62–65, 378/68, 69, 95, 97, 108, 165; 600/425–429, 600/407, 410, 411, 415–417, 436, 484, 529, 600/531–543
See application file for complete search history.

(56) References Cited

U.S. PATENT DOCUMENTS

| | | | |
|---|---|---|---|
| 5,784,431 A | 7/1998 | Kalend et al. | |
| 6,888,919 B2 | 5/2005 | Graf | |
| 7,596,283 B2 * | 9/2009 | Xu et al. | 382/294 |
| 7,649,981 B2 | 1/2010 | Seppi et al. | |
| 2004/0019274 A1 * | 1/2004 | Galloway et al. | 600/425 |
| 2005/0096515 A1 | 5/2005 | Geng | |
| 2006/0074292 A1 * | 4/2006 | Thomson et al. | 600/411 |
| 2006/0161141 A1 | 7/2006 | Chernyak | |
| 2007/0041494 A1 * | 2/2007 | Ruchala et al. | 378/65 |
| 2007/0041495 A1 * | 2/2007 | Olivera et al. | 378/65 |
| 2007/0041497 A1 * | 2/2007 | Schnarr et al. | 378/65 |
| 2007/0043286 A1 * | 2/2007 | Lu et al. | 600/407 |
| 2007/0053491 A1 | 3/2007 | Schildkraut et al. | |
| 2008/0031404 A1 * | 2/2008 | Khamene et al. | 378/6 |

FOREIGN PATENT DOCUMENTS

| | | |
|---|---|---|
| WO | 2007099525 A2 | 9/2007 |
| WO | 2007102920 A2 | 9/2007 |

OTHER PUBLICATIONS

WIPO Search Report dated Dec. 5, 2008 for PCT patent application No. PCT/US2008/077998.
Wang, H. et al., "Validation of an accelerated 'demons' algorithm for deformable image registration in radiation therapy", Institute of Physics Publishing, Physics In Medicine and Biology.
Maintz, J.B.A. et al, "A Survey of Medical Image Registation", Oxford University Press, Medical Image Analysis, 1-37.
Castro et al.: "A Cross Validation Study of Deep Brian Stimulation Targeting: From Experts to Atlas-Based, Segmentation-Based and Automatic Registration Algorithms". IEEE Transactions on Medical Imaging. vol. 25. No. 11. Nov. 2006.
Supplementary European Search Report dated Aug. 12, 2010 for Application No. EP. 08833825.

* cited by examiner

*Primary Examiner* — Edward J Glick
*Assistant Examiner* — Anastasia Midkiff
(74) *Attorney, Agent, or Firm* — Vista IP Law Group, LLP.

(57) ABSTRACT

A method includes obtaining a first image, obtaining a second image, determining a deformation field using the first and second images, and determining a transformation matrix using the deformation field. A computer product having a set of instruction, an execution of which causes a process to be performed, the process comprising determining a deformation field using first and second images, and determining a transformation matrix using the deformation field. A system includes a computer-readable medium for storing a first image and a second image, and a processor configured to determine a deformation field using the first and second images, and determine a transformation matrix using the deformation field.

31 Claims, 7 Drawing Sheets

US 7,933,380 B2

RADIATION SYSTEMS AND METHODS USING DEFORMABLE IMAGE REGISTRATION

FIELD

This application relates generally to radiation systems and methods, and more specifically, to radiation systems and methods that use deformable image registration.

BACKGROUND

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been used to obtain image of tissue for planning or treatment purposes.

During a radiation planning session, radiation treatment planning is performed before treatment radiation is delivered to a patient. This allows an accurate and precise dosage of radiation to be delivered to a patient. During the planning session, configuration data, such as location, size, and shape of a target object, may be acquired from an imaging procedure. Such imaging procedure may be performed using existing CT imaging systems, or using other types of medical imaging devices known in the art.

After the radiation treatment plan is determined, the patient then undergoes a radiation treatment procedure. During a radiation treatment procedure, a portion of the patient is imaged, and the obtained image is used to register the patient with the treatment plan. This ensures that a target location prescribed by the treatment plan corresponds with the actual target region of the patient. In some cases, the image that is obtained during the treatment procedure is compared with the reference image that is acquired during the treatment planning phase. If the result of the comparison indicates that the target region is shifted and/or rotated relative to the requirements prescribed by the treatment plan, the patient may be positioned accordingly so that the patient is correctly registered with the treatment plan. After the patient is positioned, a radiation treatment system is used to deliver a desired radiation dosage to the patient according to the determined radiation treatment plan.

Existing systems use rigid registration to register a patient with a treatment plan. Sometimes, such rigid registration may be not work, or may produce unintended result, when non-rigid component is present in the images. Rigid registration algorithms assume that patient may have translated or rotated, but not changed shape or size. For example, a target region may have shifted, rotated, changed shape, and/or changed size, since the treatment planning phase. In such cases, registering a current image of the patient (e.g., one obtained during a treatment phase) with a reference image (e.g., one obtained during the treatment planning phase) may result in the registration model being trapped into a local minimum. For example, if the distance between bone and a target region is different in images, one translation and/or rotation of one image relative to the other can not match both (the bone and the target region) well at the same time. The algorithm may get trapped into a local minimum, where images of the bone matches well, but the images of the target matches poorly, or vice versa. As such, there is a need for systems and methods for improving rigid registration in medical procedures, and more specifically, in radiation procedures.

SUMMARY

In accordance with some embodiments, a method includes obtaining a first image, obtaining a second image, determining a deformation field using the first and second images, and determining a transformation matrix using the deformation field.

In accordance with other embodiments, a computer product having a set of instruction, an execution of which causes a process to be performed, the process comprising determining a deformation field using first and second images, and determining a transformation matrix using the deformation field.

In accordance with other embodiments, a system includes a computer-readable medium for storing a first image and a second image, and a processor configured to determine a deformation field using the first and second images, and determine a transformation matrix using the deformation field.

Other aspects and features will be evident from reading the following detailed description of the embodiments.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Figure 1A:
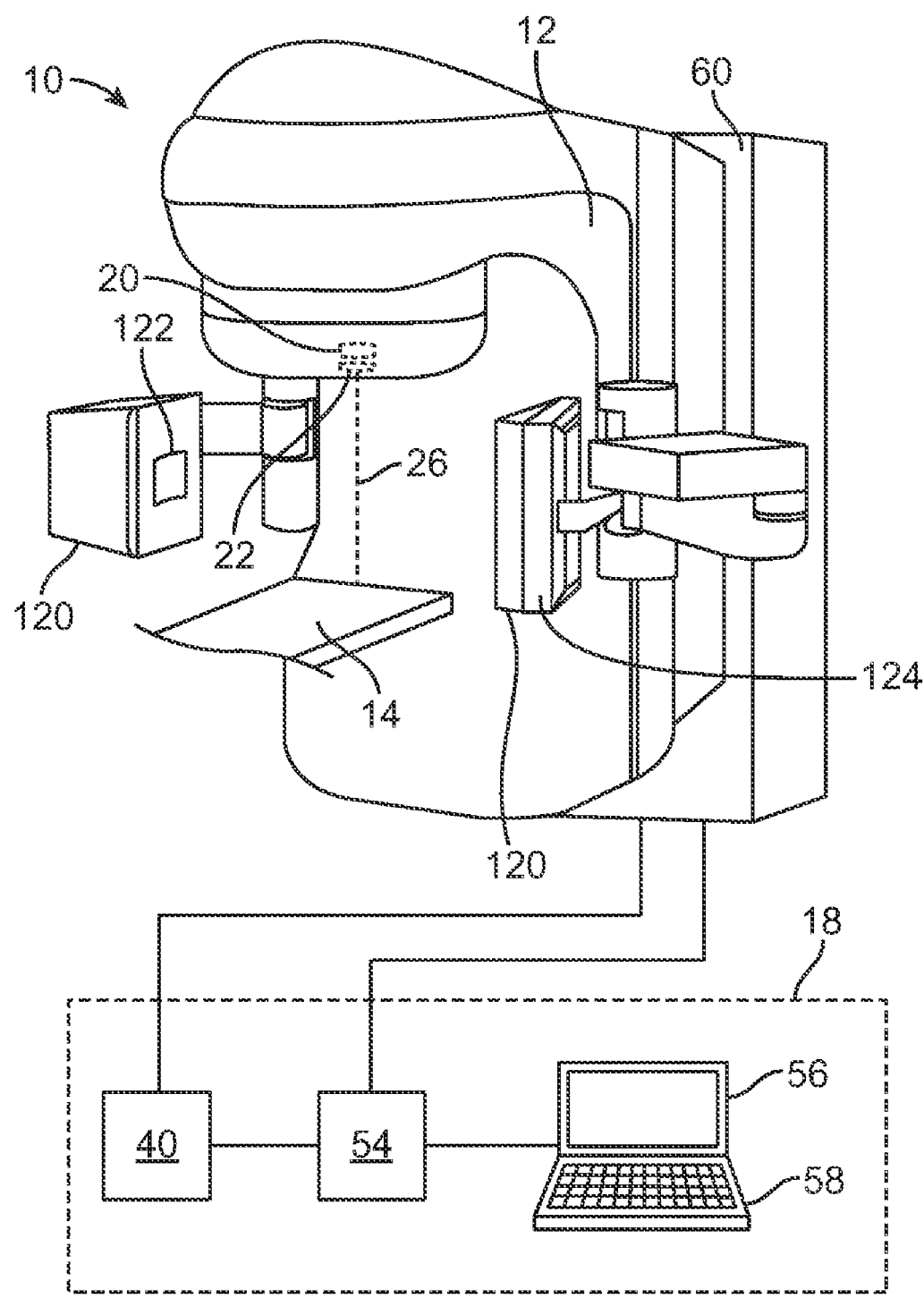
FIGS. 1A-1C illustrate different radiation systems.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments. Moreover, alternative configurations, components, methods, etc. discussed in conjunction with one embodiment can be used in any other embodiment even if such other embodiment does not discuss such alternatives or discusses different alternatives.

FIG. 1A illustrates a radiation treatment system 10 in accordance with some embodiments. The system 10 includes a gantry 12 (in the form of an arm), a patient support 14 for supporting a patient, and a control system 18 for controlling an operation of the gantry 12. The gantry 12 is rotatably coupled to a support 60. The system 10 also includes a radiation source 20 that projects a beam 26 of radiation towards the patient while the patient is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100 of FIG. 1B, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the embodiment of FIG. 1A, the radiation source 20 is coupled to the arm gantry 12. Alternatively, the radiation source 20 may be located within a bore (e.g., FIG. 1C).

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure, and the position of the radiation source 20 remains fixed relative to the patient support 14. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

Returning to FIG. 1A, the system 10 further includes an imaging system 120 having a x-ray source 122 and an imager 124. The x-ray source 122 and the imager 124 are coupled to the support 60. Alternatively, the source 122 and the imager 124 can be mounted on other structures, such as a C-arm, a mechanical linkage, or a component of the treatment system 10. During use, the x-ray source 122 emits radiation towards an object, such as a patient, and the imager 124 measures the radiation absorption at a plurality of transmission paths defined by the radiation. The imager 124 produces a voltage proportional to the intensity of incident radiation, and the voltage is read and digitized for subsequent processing in a computer, such as the processor 54, or another processor. In some embodiments, the imaging system 120 also includes a processor, such as the processor 54, for processing image data generated by the imager 124. In other embodiments, the imaging system 120 may be a CT imaging system, or other types of imaging system known in the art of medical imaging. For example, in other embodiments, the imaging system 120 may be a PET device that includes two imagers (e.g., located on respective side arms, such as those shown in FIG. 1A).

Figure 1B:
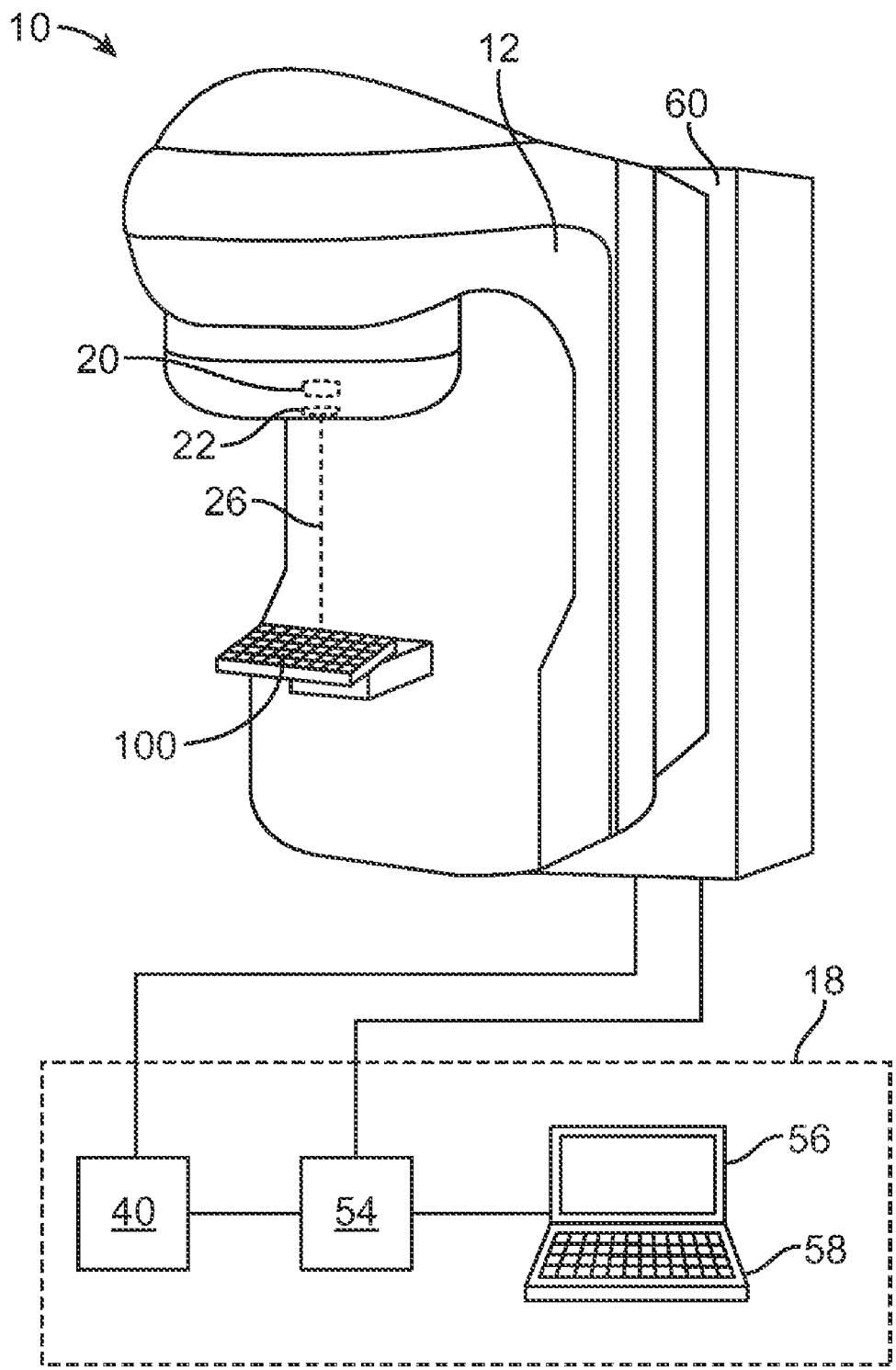

In other embodiments, if the source 20 is capable of generating diagnostic radiation beam, the system 10 does not need the imaging system 120. Instead, the system 100 may include an imager 100 located at an operative position relative to the source 20 (FIG. 1B). During a diagnostic procedure, the radiation source 20 generates and directs a radiation beam towards the patient 16, while the detector 100 measures the radiation absorption at a plurality of transmission paths defined by the radiation beam during the process. The detector 100 produces a voltage proportional to the intensity of incident radiation, and the voltage is read and digitized for subsequent processing in a computer, such as the processor 54 or another processor. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning, and/or to verify a position of a target tissue.

Figure 1C:
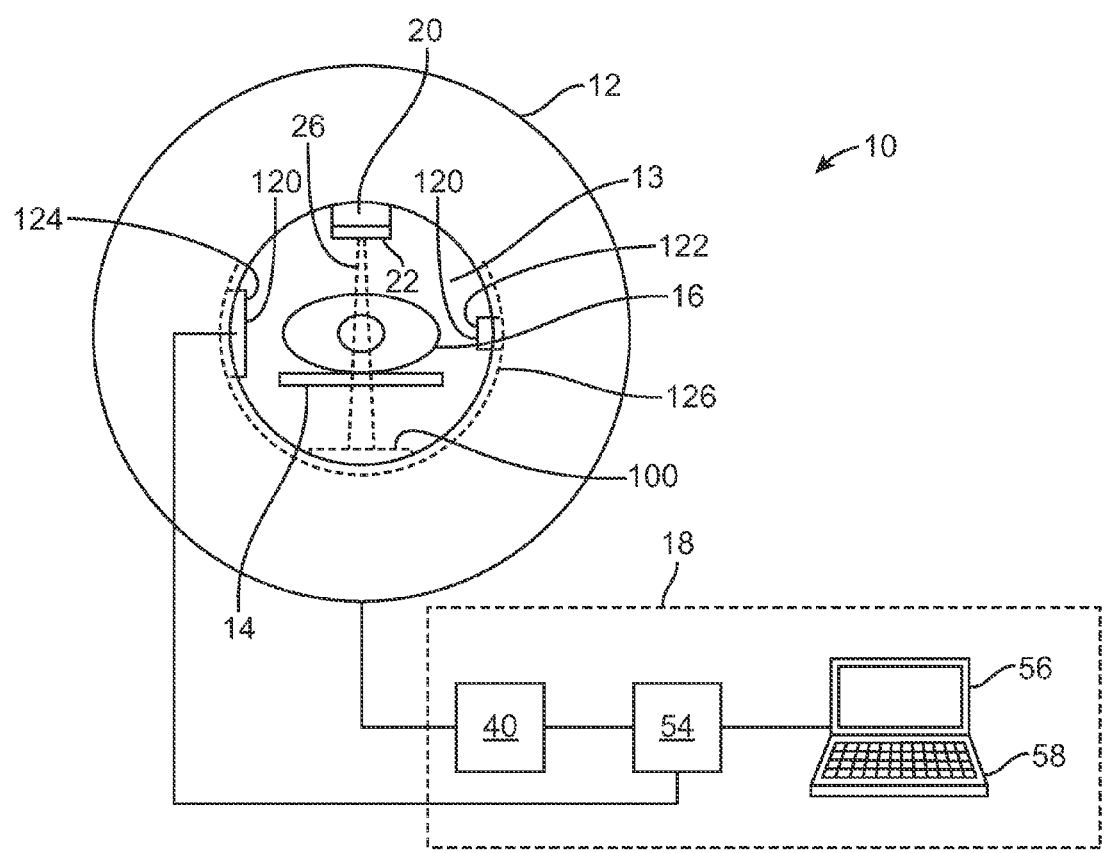

In further embodiments, the system 10 can have a different configuration. For example, the system 10 can have a gantry that is in the form of a ring (FIG. 1C). In the illustrated embodiments, the x-ray source 122 and the imager 124 are mounted to a ring 126 next to the gantry 12, wherein the ring 126 can be rotated to change a position of the imager 124 relative to a patient. The ring 126 is also moveable independent of the gantry 12, thereby allowing the x-ray source 122 to move relative to the radiation source 20.

In some embodiments, the system 10 can further include an imager 100 (shown in dotted-line in FIG. 1C) located next to the opening 13 and opposite from the radiation source 20. Such configuration allows the patient 16 to be imaged and treated without removing the patient 16 from the system 10. In some embodiments, the imager 100 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 100 can have a curvilinear surface (e.g., a partial circular arc). Such configuration is beneficial in that each of the imaging elements of the imager 100 is located substantially the same distance from the radiation source 20. In an alternative embodiment, the imager 100 may have a rectilinear surface or a surface having other profiles. The imager 100 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 100 may use different detection schemes. For example, in alternative embodiments, instead of having the conversion layer, the imager 100 may include a photoconductor, which generates electron-hole-pairs or charges in response to radiation.

It should be noted that the radiation treatment system 10 should not be limited to the configuration described previously, and that the radiation treatment system 10 can also have other configurations in other embodiments. For example, in other embodiments, instead of an L-shape arm configuration (FIGS. 1A and 1B) or a ring-configuration (FIG. 1C), the radiation treatment system 10 can have a C-arm configuration. In other embodiments, the radiation system 10 can have configurations that are known in the art of radiation systems.

Figure 2:
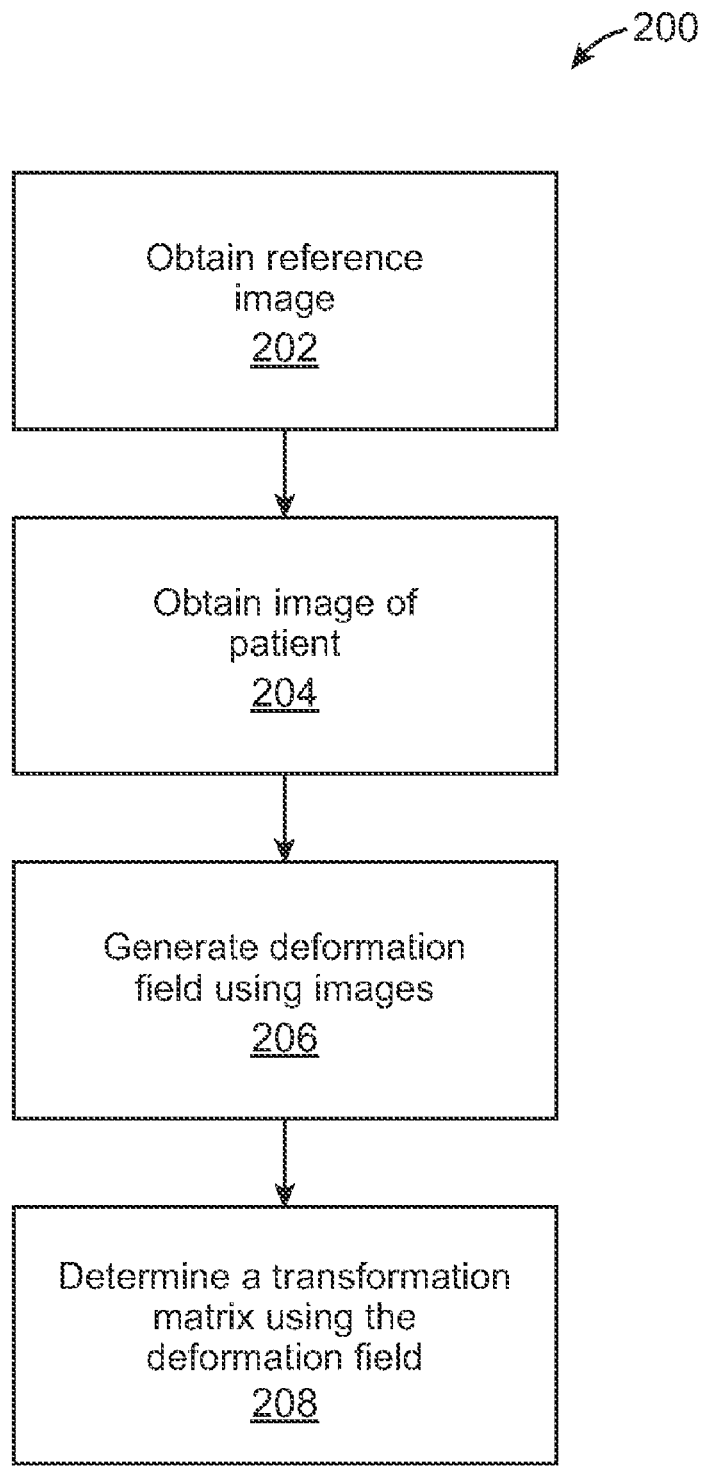
FIG. 2 illustrates a method for determining a rigid registration in accordance with some embodiments.

FIG. 2 illustrates a method 200 for obtaining a rigid registration for a patient in accordance with some embodiments. First, a reference image is obtained (Step 202). In some embodiments, the reference image may be an image of the same person for whom rigid registration is being obtained using the method 200. In such case, the reference image may be one that is obtained previously, e.g., in a different imaging session for the same patient that may have occurred on a different day, or on the same day that the method 200 is being performed. In other embodiments, the reference image may be an image of another person for whom rigid registration is not being obtained using the method 200. In further embodiments, the reference image may be an artificially created image (e.g., a model) that does not correspond to any particular individual. In any of the embodiments described herein, the reference image is stored in a computer-readable medium, which may be a long-term storage device, or a temporary memory, for later use. For example, the reference image may be stored in a hard drive or a memory associated with the processor 54, a hard drive or a memory associated with another processor (not shown), or a server.

Next, an image of a portion of a patient is obtained (Step 204). In the illustrated embodiments, the image is obtained using the radiation system 10, and is a CT image of a portion of the patient. For example, if the radiation source 20 is one that is capable of delivering diagnostic radiation, then the radiation source 20 may be used with imager 100 to obtain an image of the patient. Alternatively, the imaging system 120 may be used to obtain the image of the patient in Step 204. In other embodiments, the image may be other types of images, such as a X-ray image, a PET image, a SPECT image, a PET-CT image, or a MRI. Such image may be generated using the system 10 if the system 10 is equipped to generate such type of image. Alternatively, any of such types of image may be obtained using conventional imaging system that is known in the art of medical imaging.

After the image of a portion of the patient is obtained, a deformation field is generated using the reference image obtained in Step 202 and the image obtained in Step 204 (Step 206). The deformation field may be generated using the processor 54. Alternatively, the deformation field may be generated by another processor (not shown), e.g., a processor that is configured to receive information (e.g., image data) from the processor 54. In the illustrated embodiments, the deformation field is generated using a deformable image registration algorithm. The deformable image registration algorithm uses two images (i.e., the reference image obtained from Step 202, and the image obtained from Step 204) as input, and produces a vector field that maps each prescribed location in one image to some location in another image. The prescribed locations may be all of the pixel points in one image. Alternatively, the prescribed locations may be a subset of all points (e.g., control points) in one image. For example, the prescribed locations may be two or more points for an organ within an image. Deformable image registration algorithms are also called non-rigid registration algorithms or elastic registration algorithms, and are well known in the art of image processing.

Figure 3A:
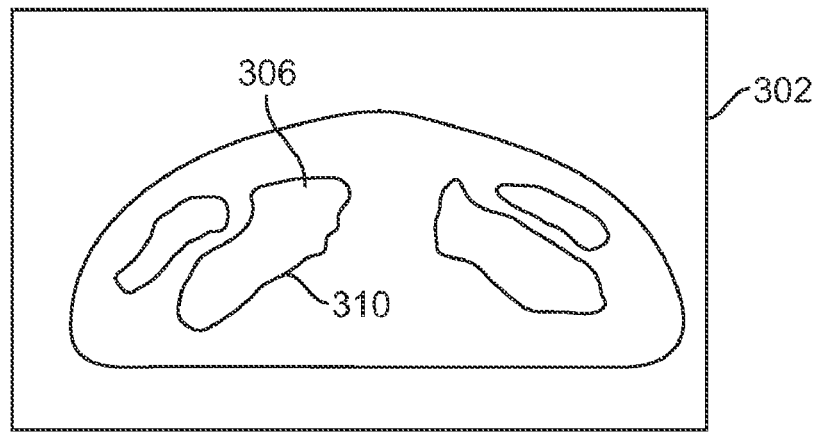
FIG. 3A illustrates an example of a reference image.
Figure 3B:
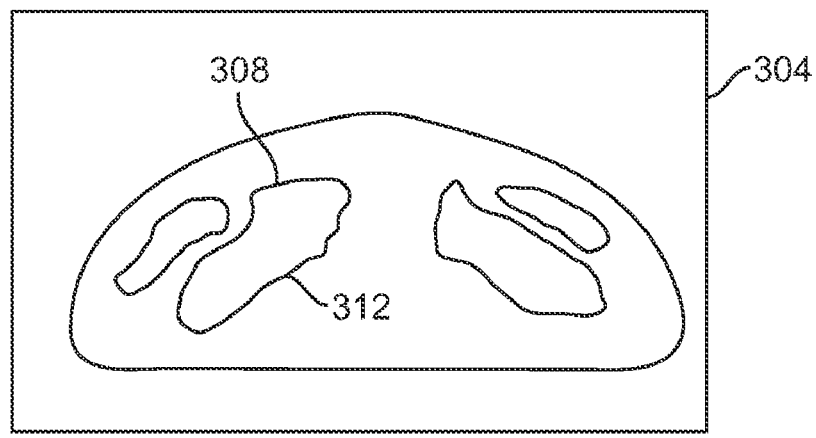
FIG. 3B illustrates an example of an image obtained for a patient.
Figure 3C:
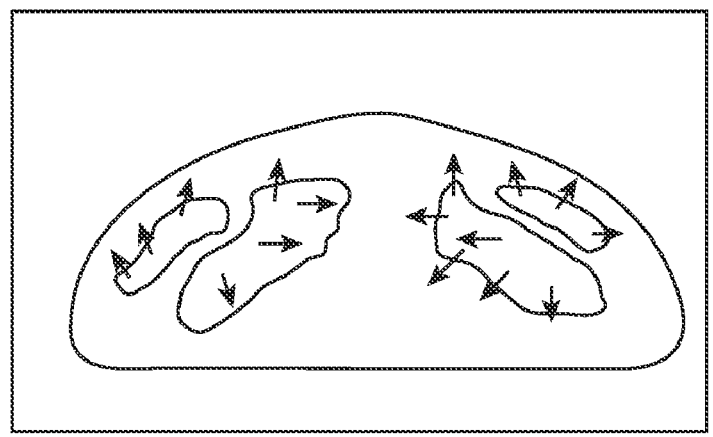
FIG. 3C illustrates an example of a vector field obtained using the image of FIG. 3A and the image of FIG. 3B.

FIG. 3A illustrates an example of a reference image 302 that may be obtained in Step 202. In the illustrated example, the reference image 302 includes an image 306 of a region 310 within a patient. FIG. 3B illustrates an example of an image 304 that may be obtained in Step 204. In the illustrated example, the image 304 includes an image 308 of a region 312 within a patient. Also, in the illustrated example, the images 302, 304 are obtained from the same patient, and the regions 310, 312 correspond to the same structure within the patient. As shown in FIGS. 3A and 3B, the structure of the patient that corresponds to regions 310, 312 has changed shape and size, and has also moved since the reference image 302 was obtained. FIG. 3C illustrates an example of a deformation field, which is a vector field that maps locations (e.g., control points) in the image of FIG. 3A to the locations in the image of FIG. 3B. Although only several vectors are shown, in some cases, the deformation field may include hundred(s), or thousand(s) of vectors. As shown in FIG. 3C, the deformation field includes a plurality of vectors, with each vector corresponding to a control point. Each vector in the deformation field has a direction that represents a direction in which a control point in the reference image 302 moves in order to reach the location as the control point appears in the image 304. Each vector in the deformation field also has a magnitude that represents a distance that a control point in the reference image 302 travels in the corresponding direction in order to reach the location as the control point appears in the image 304.

In other embodiments, instead of obtaining the reference image 302 for the same patient as that associated with image 304, the reference image 302 may be obtained from a different patient, or from a model. In such cases, the deformable image registration can be used to map a patient image to atlas patient image (different patient). For example, different regions may be predefined in the atlas patient, such as locations of different parts of a brain (e.g., brainstem, optic nerves, etc), different parts of a heart, or different parts of a lung. When the deformable image registration creates a mapping from the patient image to the atlas patient image, the physician will then know where the different parts of or an organ (e.g., brain, heart, lung) are located in the patient image, using the atlas patient image as a map.

In some embodiments, the deformable image registration algorithm uses an iterative process. In such case, the deformable image registration algorithm starts with some initial deformation field (which may be based on some known geometry in advance, or alternatively, based on initial guess). In some cases, the deformation field is presented as a matrix of displacement vectors. The deformable image registration algorithm goes through the elements of the deformation field matrix. For each element (e.g., displacement vector), the algorithm finds a change that locally improves the quality of match. The match quality can be evaluated by using some metric (e.g., mutual information and squared intensity differences may be used as metric). Mutual information is a measure known in the field of probability and information theory. It tells how much of the information is "same information" in the images. In some cases, the improvement in quality of match can be found, for example, by looking at the local derivative of the quality of match function, and by making change in the direction of derivative. The above-described process is then iterated. In some cases, the algorithm first uses a coarse grid, and then uses finer grid(s) as registration progresses. Such technique has been called "multi-resolution approach."

It should be noted that the type of deformable image registration algorithm is not limited to that described previously, and that other deformable image registration algorithms known in the art may also be used. For examples, deformable image registration algorithms have been described in "Validation of an accelerated 'demons' algorithm for deformable image registration in radiation therapy" by Wang et al., and developed at MDACC.

Returning to FIG. 2, next, the processor 54 determines a transformation matrix using the deformation vector field (Step 208). In step 208, the deformation algorithm is used to fit different regions in an image (e.g., one of the images from steps 202, 204) with different translations and/or rotations to match another image (e.g., another of the images from steps 202, 204). As such, the deformation algorithm has a holistic view of changes at different locations in an image. From these local translations and rotations, the algorithm deduces a "common" translation and rotation (the transformation matrix) that is close to the translations and rotations in different regions of the image. In some embodiments, the transformation matrix (which may be, e.g., a 4×4 matrix) contains information about rigid transformation, e.g., translation and/or rotation information. Also, in some embodiments, the transformation matrix may have less degrees of freedom than the deformation field. Such a matrix may also contain shear/scaling information.

In one technique for determining the transformation matrix, some initial guess is first generated, for example, by calculating the average of all vectors in the deformation vector field, and setting rotational parameters to "0." Next, an optimization method is then performed to find a better solution starting from the initial guess.

A variety of optimization techniques may be used to obtain the transformation matrix in Step 208. In the illustrated embodiments, the matrix is optimized using a Simplex search method. In some embodiments, the Simplex technique used is a downhill simplex method, which is also known as the Nelder-Mead method. Such optimization method is known in the art. In the Simplex method, n+1, where n is the number of degrees of freedom in search space, control points are placed in a search space. In some embodiments, an objective function may be used to evaluate how well the optimization goal is achieved. In such cases, objective function value, such as similarity measure, is then calculated for these points. The worst point is replaced by a new point by calculated by the simplex rules (Reflect the worst value through centerpoint of simplex. Calculate new objective function value for the reflected point. If the value is better than current best, calculate a new point longer away from centerpoint. If the value is bad shrink the simplex). More information about the Nelder-Mead method can be found at: http://en.wikipedia.org/wiki/Nelder-Mead_method.

In other embodiments, other known methods, such as the simulated annealing method, or the conjugate gradient method, can be used. The simulated annealing method makes a random change to a current best location, and calculates the objective function. If the calculated value for the objective function is worse, it is accepted with a probability that depends on a variable, such as temperature. In some cases, better objective function values are always accepted, and the process repeats until the value for the objective function is worse. As used in this specification, the term "temperature" needs not refer to real temperature (i.e., hotness or coldness), and may be used to refer to a variable for use in an optimization, wherein when the value of such variable is high, worse objective function values are more easily accepted. For example, a simulation may be started with a higher temperature, and then gradually be decreased to finally converge in local minimum.

The conjugated gradient method calculates the gradient of an objective function, and chooses the direction of gradient as the direction of optimization. In some cases, constraint(s) is imposed to avoid sic-sac-movement as the path of optimization, thereby improving the efficiency to obtain the optimized result.

In some embodiments, the objective function used by the optimization represents a difference metric, which indicates how good is the match between rigid transformation (e.g., which may be presented by the transformation matrix in some embodiments) and a deformable match (e.g., which may be presented by the deformation field in some embodiments). In some embodiments, the difference metric between the matrix transformation and the deformation can be a square-difference integral. For example, the objection function can be an integrated squared-difference ($|T(u)-D(u)|^2$) integral, in which T is the rigid transformation, and D(x) is the deformation field, where u goes over points of deformation field.

The transformation matrix obtained in Step 208 may be used to perform various procedures.

In some embodiments, the transformation matrix may be used to position the patient relative to the radiation source 20. For example, the transformation matrix may contain translation and rotation information required to make the images match as closely as possible. In this case, the patient support device, such as the couch where the patient is lying on, may be moved and rotated by the amount of translation and rotation, respectively, as they are represented in the matrix. As a result of this operation, the patient geometry matches better with the planning geometry. For such purpose, in any of the embodiments described herein, the system 10 may include, or used with, a patient support (e.g., patient support 14) that can translate in two or more directions. For example, in some embodiments, the patient support may translate along the z-direction (its longitudinal axis), and along a y-direction (e.g., a lateral direction). In further embodiments, the patient support may further translate along a third direction, e.g., in a vertical direction. In such cases, moving the patient support can provide corrective translations of the target. Patient supports having multiple of degrees of freedom are known in the art, and therefore, would not be described in further detail. After the patient is desirably positioned, the system 10 is then used to deliver treatment radiation to the patient to treat the patient.

In some embodiments, the transformation matrix may be used to change the treatment plan. For example, the radiation fluences from different radiation directions may be spatially scaled using the information from the transformation matrix.

The above described technique is advantageous because the method does not get trapped in local minima as easily as prior art models. Also, in some cases, using the above described technique can generate a good match between images even when there are small distortions from a rigid match.

Figure 4:
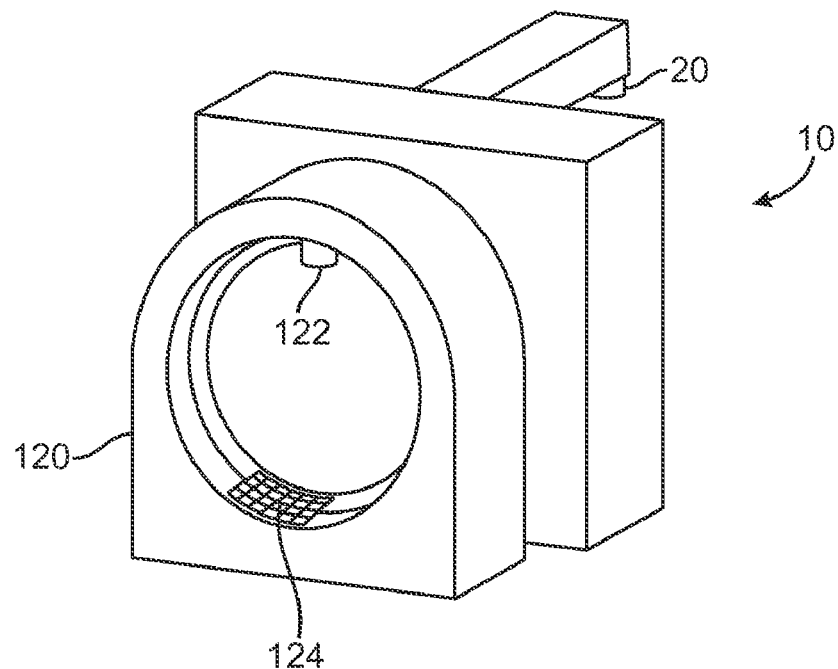
FIG. 4 illustrates another radiation system in accordance with other embodiments.
Figure 5:
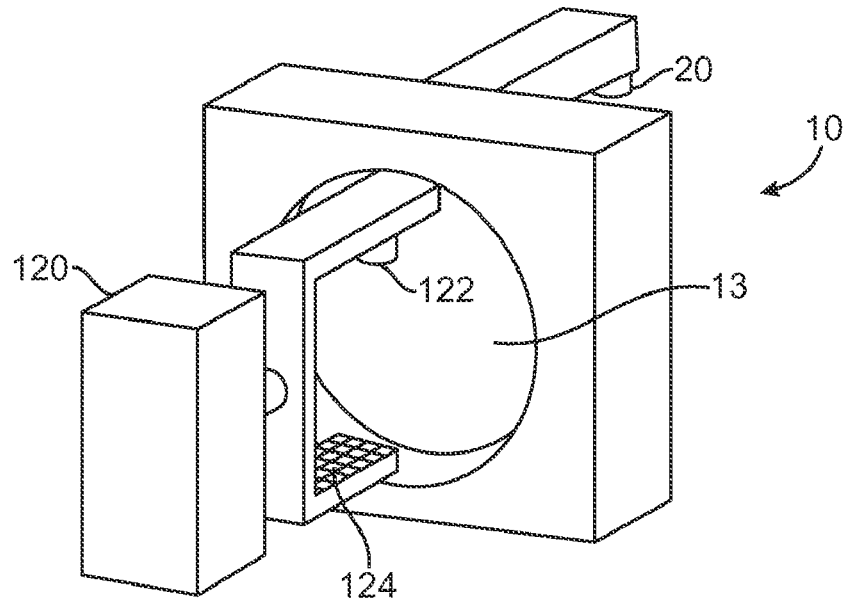
FIG. 5 illustrates another radiation system in accordance with other embodiments.

It should be noted that the system 10 is not limited to the examples described previously, and that the system 10 can have other configurations in other embodiments. For example, in other embodiments, the system 10 is implemented using a diagnostic machine and a treatment machine, wherein the diagnostic machine includes the x-ray source 122 and the imager 124, and is a separate component from the treatment machine (FIG. 4). The diagnostic machine may be different diagnostic devices in different embodiments. For examples, the diagnostic machine may be a laminar tomography device, a MRI device, a fluoroscope, an angiography device, a PET device (which may include two imagers, or a single imager with a ring configuration), a SPECT device, a PET-CT device, a tomosynthesis imaging device, a CT device, a CBCT device, etc. In further embodiments, any of these diagnostic devices or any multiple combination of these diagnostic devices may be integrated with a treatment machine to form the radiation system 10. In other embodiments, the imaging system 120 can have a C-arm configuration (FIG. 5). In further embodiments, the x-ray source 122 and imager 124 of the imaging system 120 do not move in a circular (or partial circular) motion. For example, the x-ray source 122 can be configured to move in a translational motion. In other embodiments, the source 122 is configured to move in a plane that is parallel to the imager plane. Other types of source-imager relative motion may also be used in other embodiments.

Also, in any of the embodiments described herein, the system 10 can include a through bore, such as the bore 13 shown in FIG. 5.

Computer System Architecture

Figure 6:
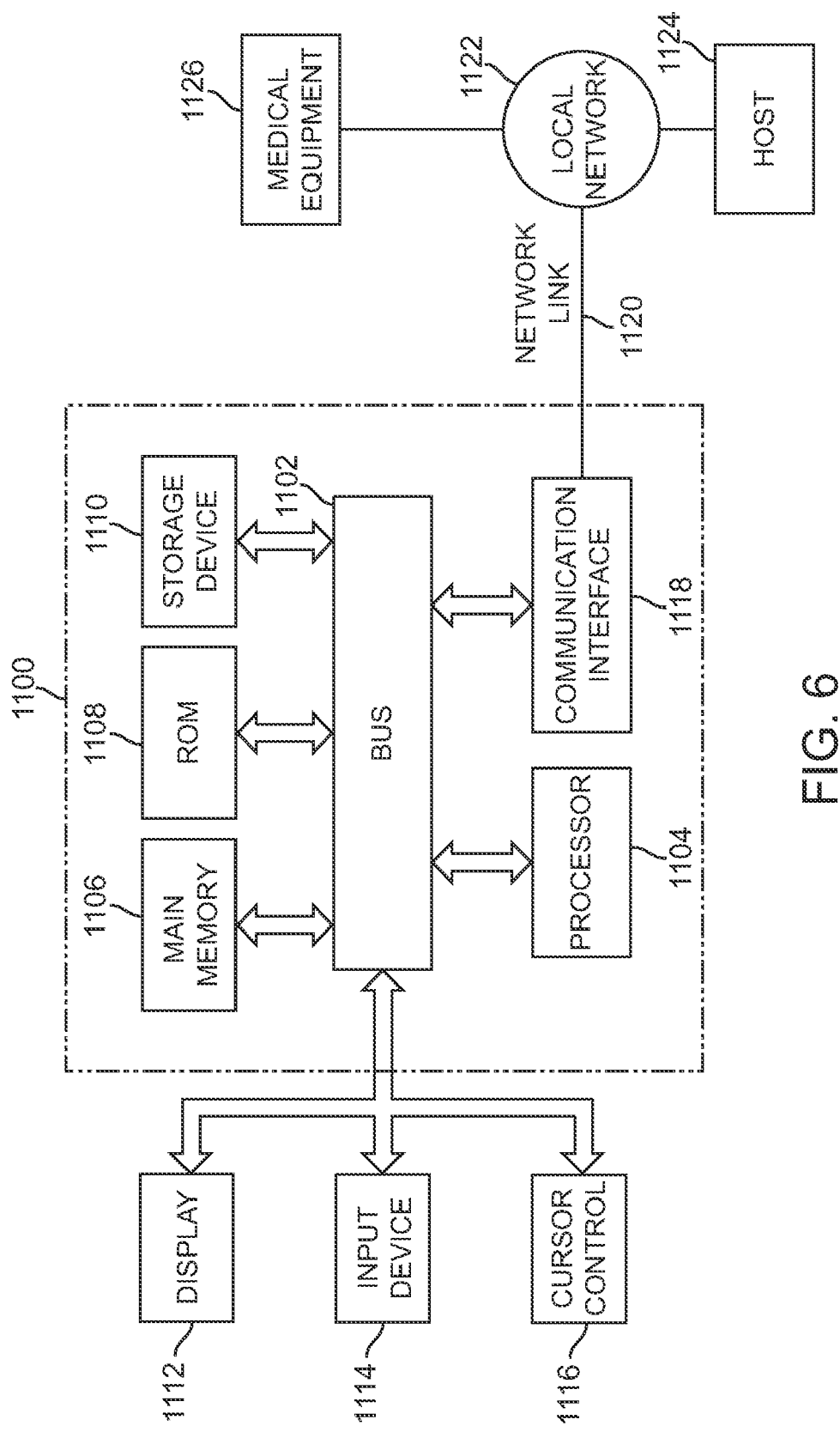
FIG. 6 illustrates a block diagram of a computer system that can be used to control an operation of a radiation system in accordance with some embodiments.

FIG. 6 is a block diagram illustrating an embodiment of a computer system 1100 that can be used to implement various embodiments of the method described herein. Computer system 1100 includes a bus 1102 or other communication mechanism for communicating information, and a processor 1104 coupled with the bus 1102 for processing information. The processor 1104 may be an example of the processor 114, or alternatively, an example of a component of the processor 114. The computer system 1100 also includes a main memory 1106, such as a random access memory (RAM) or other dynamic storage device, coupled to the bus 1102 for storing information and instructions to be executed by the processor 1104. The main memory 1106 also may be used for storing temporary variables or other intermediate information during execution of instructions to be executed by the processor 1104. The computer system 1100 further includes a read only memory (ROM) 1108 or other static storage device coupled to the bus 1102 for storing static information and instructions for the processor 1104. A data storage device 1110, such as a magnetic disk or optical disk, is provided and coupled to the bus 1102 for storing information and instructions.

The computer system 1100 may be coupled via the bus 1102 to a display 1112, such as a cathode ray tube (CRT), or a flat panel display, for displaying information to a user. An input device 1114, including alphanumeric and other keys, is coupled to the bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane.

In some embodiments, the computer system 1100 can be used to perform various functions described herein. According to some embodiments of the invention, such use is provided by computer system 1100 in response to processor 1104 executing one or more sequences of one or more instructions contained in the main memory 1106. Those skilled in the art will know how to prepare such instructions based on the functions and methods described herein. Such instructions may be read into the main memory 1106 from another computer-readable medium, such as storage device 1110. Execution of the sequences of instructions contained in the main memory 1106 causes the processor 1104 to perform the process steps described herein. One or more processors in a multi-processing arrangement may also be employed to execute the sequences of instructions contained in the main memory 1106. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1104 for execution. Such a medium may take many forms, including but not limited to, non-volatile media, volatile media, and transmission media. Non-volatile media includes, for example, optical or magnetic disks, such as the storage device 1110. Volatile media includes dynamic memory, such as the main memory 1106. Transmission media includes coaxial cables, copper wire and fiber optics, including the wires that comprise the bus 1102. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1104 for execution. For example, the instructions may initially be carried on a magnetic disk of a remote computer. The remote computer can load the instructions into its dynamic memory and send the instructions over a telephone line using a modem. A modem local to the computer system 1100 can receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1106, from which the processor 1104 retrieves and executes the instructions. The instructions received by the main memory 1106 may optionally be stored on the storage device 1110 either before or after execution by the processor 1104.

The computer system 1100 also includes a communication interface 1118 coupled to the bus 1102. The communication interface 1118 provides a two-way data communication coupling to a network link 1120 that is connected to a local network 1122. For example, the communication interface 1118 may be an integrated services digital network (ISDN) card or a modem to provide a data communication connection to a corresponding type of telephone line. As another example, the communication interface 1118 may be a local area network (LAN) card to provide a data communication connection to a compatible LAN. Wireless links may also be implemented. In any such implementation, the communication interface 1118 sends and receives electrical, electromagnetic or optical signals that carry data streams representing various types of information.

The network link 1120 typically provides data communication through one or more networks to other devices. For example, the network link 1120 may provide a connection through local network 1122 to a host computer 1124 or to equipment 1126, or a switch operatively coupled to any of the devices described herein. The data streams transported over the network link 1120 can comprise electrical, electromagnetic or optical signals. The signals through the various networks and the signals on the network link 1120 and through the communication interface 1118, which carry data to and from the computer system 1100, are exemplary forms of carrier waves transporting the information. The computer system 1100 can send messages and receive data, including program code, through the network(s), the network link 1120, and the communication interface 1118.

Although particular embodiments of the present inventions have been shown and described, it will be understood that it is not intended to limit the present inventions, and it will be obvious to those skilled in the art that various changes and modifications may be made without departing from the spirit and scope of the present inventions. For example, the term "image" or "image data" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method, comprising:
   obtaining a first image;
   obtaining a second image;
   determining a deformation field using the first and second images;
   determining a transformation matrix using the deformation field; and
   storing the transformation matrix;
   wherein the transformation matrix is determined using a processor, and a number of degrees of freedom associated with the transformation matrix is less than a number of degrees of freedom associated with the deformation field.

2. The method of claim 1, further comprising changing a relative position between at least a portion of a patient and a radiation source based on the transformation matrix.

3. The method of claim 2, wherein the act of changing the relative position comprises positioning a patient support.

4. The method of claim 2, wherein the act of changing the relative position comprises positioning a radiation source.

5. The method of claim 1, further comprising adjusting a treatment plan using the transformation matrix.

6. The method of claim 5, wherein the treatment plan comprises a radiation treatment plan.

7. The method of claim 1, further comprising storing the transformation matrix in a computer-readable medium.

8. The method of claim 1, wherein the transformation matrix comprises a vector.

9. The method of claim 8, wherein the vector has a direction that represents a direction of travel by a control point in the first image in order to reach a location of the control point in the second image.

10. The method of claim 8, wherein the vector has a magnitude that represents a distance between a control point in the first image and the control point in the second image.

11. The method of claim 1, wherein the first image and the second image are images of a portion of the patient.

12. The method of claim 1, wherein the first image comprises an image of another patient, and the second image comprises an image of the patient.

13. The method of claim 1, wherein the transformation matrix includes information associated with a deformation of an object.

14. The method of claim 13, wherein the transformation matrix also includes information associated with a translation and a rotation of the object.

15. A computer product having a set of instruction, an execution of which causes a process to be performed, the process comprising:
    determining a deformation field using first and second images; and
    determining a transformation matrix using the deformation field;
    wherein a number of degrees of freedom associated with the transformation matrix is less than a number of degrees of freedom associated with the deformation field.

16. The computer product of claim 15, wherein the process further comprises changing a relative position between at least a portion of a patient and a radiation source based on the transformation matrix.

17. The computer product of claim 15, wherein the process further comprises adjusting a treatment plan using the transformation matrix.

18. The computer product of claim 15, wherein the transformation matrix comprises a vector.

19. The computer product of claim 18, wherein the vector has a direction that represents a direction of travel by a control point in the first image in order to reach a location of the control point in the second image.

20. The computer product of claim 18, wherein the vector has a magnitude that represents a distance between a control point in the first image and the control point in the second image.

21. The computer product of claim 18, wherein the transformation matrix includes information associated with a deformation of an object.

22. The computer product of claim 21, wherein the transformation matrix also includes information associated with a translation and a rotation of the object.

23. A system, comprising:
    a computer-readable medium for storing a first image and a second image; and
    a processor configured to determine a deformation field using the first and second images, and determine a transformation matrix using the deformation field, wherein a number of degrees of freedom associated with the transformation matrix is less than a number of degrees of freedom associated with the deformation field.

24. The system of claim 23, wherein the transformation matrix includes information associated with a deformation of an object.

25. The system of claim 24, wherein the transformation matrix also includes information associated with a translation and a rotation of the object.

26. The method of claim 1, wherein the transformation matrix comprises a two dimensional matrix.

27. The method of claim 1, wherein the first image is obtained for a portion of a patient when the portion of the patient is stationary.

28. The computer product of claim 15, wherein the transformation matrix comprises a two dimensional matrix.

29. The computer product of claim 15, wherein the first image is obtained for a portion of a patient when the portion of the patient is stationary.

30. The system of claim 23, wherein the transformation matrix comprises a two dimensional matrix.

31. The system of claim 23, wherein the first image is obtained for a portion of a patient when the portion of the patient is stationary.

* * * * *